(12) United States Patent
Randlov et al.

(10) Patent No.: US 7,722,535 B2
(45) Date of Patent: May 25, 2010

(54) APPARATUS AND METHOD FOR ASSISTING IN CHOOSING A SITE FOR A SKIN INVASIVE ACTION

(75) Inventors: Jette Randlov, Vaerlose (DK); Ulrik Detlef Radisch Poulsen, Hillerod (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/792,730

(22) PCT Filed: Dec. 5, 2005

(86) PCT No.: PCT/EP2005/013002

§ 371 (c)(1),
(2), (4) Date: Dec. 5, 2007

(87) PCT Pub. No.: WO2006/061169

PCT Pub. Date: Jun. 15, 2006

(65) Prior Publication Data

US 2008/0139900 A1    Jun. 12, 2008

Related U.S. Application Data

(60) Provisional application No. 60/637,933, filed on Dec. 21, 2004.

(30) Foreign Application Priority Data

Dec. 8, 2004    (EP)    .................................. 04078336

(51) Int. Cl.
*A61B 5/00*    (2006.01)
(52) U.S. Cl. ...................................... 600/306; 600/300
(58) Field of Classification Search ................. 600/300, 600/306, 407
See application file for complete search history.

(56) References Cited

U.S. PATENT DOCUMENTS

| | | | |
|---|---|---|---|
| 5,865,744 A | 2/1999 | Lemelson | |
| 6,074,364 A | 6/2000 | Paul | |
| 6,156,008 A | 12/2000 | Castellano | |
| 6,305,381 B1 | 10/2001 | Weijand et al. | |
| 2001/0051774 A1* | 12/2001 | Littrup et al. | 600/547 |
| 2003/0050558 A1* | 3/2003 | Bencini et al. | 600/425 |

FOREIGN PATENT DOCUMENTS

| | | |
|---|---|---|
| EP | 1177802 | 2/2002 |
| GB | 2202445 | 9/1988 |
| WO | WO 93/02720 | 2/1993 |

* cited by examiner

*Primary Examiner*—Charles A Marmor, II
*Assistant Examiner*—Christian Y Jang
(74) *Attorney, Agent, or Firm*—Wesley A. Nicolas; Marc A. Began; Reza Green

(57) ABSTRACT

Apparatus and method for assisting in choosing a suitable site for a skin invasive action, such as drug injection, e.g. insulin for persons with diabetes, or collecting blood or tissue samples. Measures and processes parameters relating to a specific area part of the skin or subcutis and determines whether the area part is suitable for the skin invasive action based on the processed parameters. Suitable for assisting a person in choosing a site during an injection/sampling procedure, ensuring that skin invasive actions are performed at suitable sites only. Very useful for repetitive skin invasive actions, such as BG measurements and insulin injections. Helps in varying sites for the skin invasive action without the need for keeping a record of used sites manually. Helps in avoiding tissue infiltrations and lipodystrophy.

31 Claims, 4 Drawing Sheets

APPARATUS AND METHOD FOR ASSISTING IN CHOOSING A SITE FOR A SKIN INVASIVE ACTION

CROSS-REFERENCE TO RELATED APPLICATIONS

This application is a 35 U.S.C. §371 national stage application of International Patent Application PCT/EP2005/013002 (published as WO 2006/061169), filed Dec. 5, 2005, which claimed priority of European Patent Application 04078336.7, filed Dec. 8, 2004; this application further claims priority under 35 U.S.C. §119 of U.S. Provisional Application 60/637,933, filed Dec. 21, 2004.

FIELD OF THE INVENTION

The present invention relates to an apparatus and a method for assisting in choosing a site for a skin invasive action. In particular, the apparatus and method of the present invention are adapted to determine whether or not a particular area part of the skin of a mammal is suitable for the skin invasive action.

BACKGROUND OF THE INVENTION

When a skin invasive action is to be performed it is important that the site which is chosen for the action is a suitable one. This is particularly important if the skin invasive action is of a kind which needs to be repeated. Examples of such actions are repetitive injections of drugs, e.g. insulin for people with diabetes, repetitive collection of blood samples, tissue samples, such as samples from subcutaneous layers, or samples of other kinds of body fluids. This may, e.g., include blood glucose measurements for people with diabetes. When a particular area of the skin has been subject to a skin invasive action, that area will, for some time, be unsuitable for another skin invasive action of the same kind.

Thus, multiple skin invasive actions into the same spot within a relatively short period of time may cause alterations to the fat, also known as 'lipodystrophy'. This can lead to a thickening of the fat at the site of the skin invasive action and can cause lumps or slumps in the skin. In case the skin invasive action is the injection of a drug, a thickening of the fat at the site may alter the drug absorption at the site, thereby causing an unknown and uncontrollable dose of the drug to be absorbed. Furthermore, in case the person in question sometimes injects the drug in a site which is damaged and sometimes in a site which is not damaged, the absorbed amount of drug will vary from one injection to the other, thereby causing undesirable fluctuations in the absorbed amount of drug. For instance injecting insulin into the same spot too frequently can cause lipodystrophy, and thereby potentially alter the insulin absorption as described above. This may be dangerous and potentially lethal. In case the skin invasive action is collection of blood samples or tissue samples it is also undesirable to perform the action in a site which has recently been used for another skin invasive action of the same kind because the skin or one or more of the subcutaneous layers will suffer damage, at least temporarily, when a sample is collected, and scar tissue may be formed making it more difficult to penetrate the skin.

It is therefore desirable to organize repetitive skin invasive actions in such a way that the sites used for the actions is circulated in such a way that use of a site which has previously been used within a relatively short period of time is avoided.

To this end mechanical systems have previously been developed for guiding a person in choosing a site for a repetitive skin invasive action. Such a system is disclosed in GB 2 202 445 which discloses a double sided flexible injection guide grid having a number of apertures each clearly identified or defined which aids a person requiring frequent subcutaneous injections to vary the site of the injection and thus avoid complications which sometimes occur when frequent injections are given into the same small area of skin. The injection guide grid is positioned at the injection site (e.g. the stomach area of a person) and an injection is given in an area corresponding to one of the apertures. The person has to fill in a separate record card in order to keep track of which apertures have been used for injections recently, thereby avoiding that an injection is performed into a site which has recently been used for an injection. However, the injection guide grid disclosed in GB 2 202 445 is rather cumbersome to use because the person has to keep track of the injection sites in a separate record card, and there is therefore a risk that the person forgets or does not bother to fill in the record card after an injection has been performed. Furthermore, the fact that the record card has to be filled in by a person introduces the risk of human errors, i.e. the risk that the person simply fills in the record card in an erroneous manner, thereby introducing the risk that the same site is used for the next injection. Furthermore, the injection guide grid is a very inaccurate way of keeping track of the injections, and it is only possible to keep track of one body part at a time.

WO 93/02720 discloses an automatic programmable injection/aspiration device for administration of medicaments. The device comprises means for controlling the rate, direction and extent of needle insertion, fluid injection and needle withdrawal. The device is adapted to interrogate the injection site in order to ensure that the injection is performed at a desired site, i.e. in a correct kind of tissue, in order to avoid that pharmaceutical substances or other fluids are not unintentionally injected into a blood vessel, a lymph vessel or into cerebrospinal fluid. To this end an attempted aspiration is made in order to interrogate the injection site (i.e., essentially, as understood in the art the volume of tissue immediately adjacent to and in fluid communication with the open end of the needle) for the presence of blood, lymph, cerebrospinal fluid, or the like. Thus, the interrogation is performed in an invasive manner, i.e. it is performed after the device has penetrated the skin of the person, and it is therefore not possible to avoid the problems related to choosing an appropriate area part of the skin mentioned above.

U.S. Pat. No. 5,865,744 discloses a method and a system for internally delivering a therapeutic agent to a patient under the automatic control of a computer. A scanning system generates one or more images of the patient's anatomy showing an anatomical region into which it is desired to deliver the agent. Based on the image(s) a desired site, typically a tumour, for an invasive action is located, and the injection needle is moved to inject the drug exactly at the desired site.

U.S. Pat. No. 6,156,008 discloses an injection site locating device including a sensor to detect and give an indication of a suitable injection site to minimise creation of subdermal hematomas from injection of the liquid medication by the injector. In particular, the sensor detects the presence of high and/or low blood flows and indicates that a suitable injection site is over the low blood flow.

The devices disclosed in U.S. Pat. No. 5,865,744 and U.S. Pat. No. 6,156,008 are not concerned with assisting a person in choosing a site for a skin invasive action in such a manner that the problems arising from repetitive skin invasive actions described above are avoided.

SUMMARY OF THE INVENTION

It is, thus, an object of the present invention to provide an apparatus for assisting in choosing a site for a skin invasive action in such a way that an appropriate area of the skin is chosen for the action before the skin invasive action is performed.

It is a further object of the present invention to provide an apparatus for assisting in choosing a site for a skin invasive action, where the choice can be made in a non-invasive manner.

It is an even further object of the invention to provide an apparatus for assisting in choosing a site for a skin invasive action, where the risk of human errors is minimised.

It is an even further object of the present invention to provide an apparatus for assisting in choosing a site for a skin invasive action, where the site is chosen in an accurate manner.

It is an even further object of the present invention to provide an apparatus for assisting in choosing a site for a skin invasive action which is easy to use and in which manual record keeping is avoided.

Thus, according to a first aspect of the present invention the above and other objects are fulfilled by providing an apparatus for assisting in choosing a site for a skin invasive action, the apparatus comprising:

means for measuring one or more parameters relating to a particular area part of the skin or subcutis of a mammal, means for processing said parameter(s), means for categorising the particular area part based on the processed parameter(s), and means for determining whether or not the particular area part is suitable for the skin invasive action based on the processed parameter(s).

According to a second aspect of the present invention the above and other objects are fulfilled by providing a method for choosing a site for a skin invasive action, the method comprising the steps of:

measuring one or more parameters relating to a particular area part of the skin or subcutis of a mammal, processing said parameter(s), categorising the particular area part based on the processed parameter(s), and determining whether or not the particular area part is suitable for the skin invasive action based on the processed parameter(s).

It should be noted that the skilled person would readily recognise that any feature described in relation to the first aspect of the present invention may also be combined with the second aspect of the present invention, and vice versa.

The apparatus and method of the present invention are adapted to assist in choosing a site for a skin invasive action. The site should be understood as a site of the skin, i.e. the site is chosen before the skin invasive action is performed. Thereby a site which is not suitable can be discarded before the skin invasive action is performed, and it is thereby ensured that the skin invasive action is performed at a suitable site, and with least possible inconveniency for the subject.

In the present context the term 'skin invasive action' should be interpreted to mean an action which causes a physical object, e.g. a needle, a fluid, a drug and/or any other suitable kind of object to cross a boundary defined by an outer surface of the skin of the mammal. This will be described in further detail below.

The particular area part of the skin or subcutis may typically be a site which is suggested for the skin invasive action. Parameter(s) relating to the area part is/are then measured and processed in order to determine whether or not the suggested site is suitable for the skin invasive action. In case it is determined that the site for some reason is not suitable, another site will typically be suggested and the procedure will be repeated accordingly until a suitable site is found. If, on the other hand, it is determined that the site is suitable, the skin invasive action can subsequently be performed at the suggested site. The parameter(s) need not relate to the outer surface of the skin, but may alternatively or additionally relate to one or more layers positioned beneath the outer surface of the skin. This will be described in further detail below.

Whether or not the particular area part is deemed suitable for the skin invasive action may depend on a number of factors, including, but not limited to, the kind of skin invasive action, properties of an outer surface of the skin, ability of one or more subcutaneous layers to absorb a specific drug, distance to blood vessels, whether or not the site has been used recently for a similar skin invasive action, etc. The parameter(s) to be measured is/are typically selected in such a way it/they appropriately reflect(s) the properties which are important when determining whether or not the area part is suitable for the specific skin invasive action which it is intended to perform. Thus, in case the skin invasive action is of a repetitive kind as described above, the site will only be appropriate if it has not been used for a similar skin invasive action within a specific time period preceding the present time. In case the skin invasive action includes the delivery of a drug, the site will be suitable if the relevant subcutaneous layers are capable of absorbing the drug in an acceptable manner.

The apparatus further comprises means for categorising the particular area part based on the processed parameter(s). The characteristics of the skin and/or one or more subcutaneous layers of a person vary between various body parts. Thus, the skin of a stomach area of a person will be distinguishable from the skin of the thighs of the same person, primarily because the position of the subcutaneous fat layer is different for a stomach area and a thigh area. Furthermore, some characteristics of the skin and/or one or more subcutaneous layers may vary across a specific body part. Thus, the skin of an inner part of a thigh may be distinguishable from the skin of an outer part of the same thigh. Furthermore, the skin of a specific person may comprise specific and unique features which are characteristic for a specific site of the skin of that person. Such specific features may, e.g., be birth marks, lumps or slumps in the skin, damaged areas of the skin and/or subcutaneous layers, the positions of one or more inner organs, thickness of a layer of fat or variations in the thickness of a layer of fat, etc.

The means for categorising the particular area part is preferably adapted to determine to which body part the particular area part belongs (e.g. stomach or thigh). Furthermore, it is preferably adapted to determine to which part of the body part the particular area part belongs (e.g. inner thigh or outer thigh, lower part of thigh or upper part of thigh, left or right part of the stomach, e.g. based on the position of one or more inner organs). Alternatively or additionally, the categorising means may be adapted to identify the particular area part, i.e. the categorising means may be adapted to determine exactly which part of the skin of the mammal in question the particular area part is. Such an identification of the particular area part may be based on a comparison between the measured and processed parameter(s) on one hand and previously obtained data on the other hand. In this case the apparatus preferably comprises or is connected to a storage device where previously obtained data is stored. For each area which has previously been investigated a record of the measured and/or the processed parameter(s) may be stored, preferably along with relevant information, such as information relating to when the area part was last used for a skin invasive action. When an area part is suggested for a skin invasive action, the processed parameter(s) is/are compared to the information which is stored in the storage device. In case the processed parameter(s) of the suggested area part fully or partly match(es) corresponding processed parameter(s) belonging to an area part for which data is stored in the storage device, it is very likely that the two area parts are in fact the same. The area part has thereby been identified.

This identification can then be used for determining whether or not sufficient time has elapsed since the area part was last used for a skin invasive action to make the area part suitable for another skin invasive action. Based on this the area part may be deemed suitable or unsuitable.

The apparatus may also comprise means for suggesting another site for the skin invasive action in case it is determined that the particular area part is unsuitable for the skin invasive action, or that another site is better suited for the skin invasive action. For example, in case the skin invasive action is injection of a dose of insulin to a mammal with diabetes, it may be known that the action of the insulin is needed as fast as possible, e.g. in order to lower a too high blood glucose level. In case the particular area part is categorised as a thigh, the apparatus may suggest that a stomach part is chosen instead, as the insulin is absorbed faster from the stomach than from the thigh.

The fact that a particular area part of the skin or subcutis of the mammal is investigated in respect of a number of parameters, and the fact that the suggested site is accepted or rejected for the skin invasive action on the basis of the measured and processed parameter(s) makes it possible to choose the site for the skin invasive action before the skin invasive action is actually performed. Thereby the site can be chosen in such a way that any unsuitable site will be rejected, and in such a way that the disadvantages related to repetitive skin invasive action described above can be avoided, or at least considerably reduced. Furthermore, the apparatus and method of the present invention are very suitable for helping a person with a need for repetitive skin invasive actions, e.g. a person with diabetes, in keeping track of the sites used, thereby enabling that person to vary the chosen sites in a recommended manner without requiring cumbersome manual actions of the person.

The apparatus may further comprise means for indicating whether or not the particular area part is suitable for the skin invasive action. Such means may include a display screen for showing the result to a user of the apparatus. Alternatively or additionally it may include a sound generator for generating an audible signal indicating to the user whether or not the area part is suitable for the skin invasive action, e.g. by means of two distinctive sounds. Alternatively or additionally, the indicating means may include a vibrator or the like causing the apparatus or a part of the apparatus to vibrate, thereby indicating to the user that the area part is suitable or that the area part is not suitable.

The indicating means may comprise means for producing a warning signal in case it is determined that the particular area part is not suitable for the skin invasive action. Such a warning signal may be visible, audible and/or adapted to be sensed by touch as described above. Thus, it may comprise a display screen, a loudspeaker, a vibrator, etc. The indicating means may further be adapted to indicate why it has been determined that an area part is unsuitable, e.g. whether it is due to damaged tissue, inappropriate absorption characteristics, the area has been used recently, etc. In this case the indicating means preferably comprises a display screen for communicating this information to the user. In case the particular area part is deemed unsuitable because it has been used too recently for a previous skin invasive action, the warning signal may be followed by a message informing the user of when, or at least approximately how long ago, the area part was last used for a skin invasive action.

The processing means may comprise means for comparing at least some of the measured parameter(s) to one or more previously measured corresponding parameters. This may advantageously be used for categorising or identifying the particular area part as described above. Thus, on the basis of such a comparison it may be determined that the area part belongs to a specific body part of the mammal, or even that it belongs to a specific part of a specific body part. Furthermore, the precise location may be determined, e.g. based on specific characteristics of that mammal, e.g. birth marks, skin texture or colouring, lumps or slumps of the skin, distribution of subcutaneous layers, thickness and/or distribution of a layer of fat, areas of damaged tissue, etc.

The processing means may function as a neural network, i.e. it may be adapted to be 'trained' in such a way that it will be able to recognise special features of the skin and/or one or more subcutaneous layers and/or one or more boundaries between such layers for a specific person. The apparatus may thereby, after a while, be able to distinguish between normal tissue and damaged tissue for that person. Since 'normal tissue' may vary from person to person an apparatus as described will be able to distinguish more accurately between normal tissue and damaged tissue than would be the case if average reference parameters were used. The training of the processing means may, e.g., be performed initially, e.g. by scanning a number of relevant sites for the skin invasive action in order to let the apparatus record and store characteristics of the individual sites. When the apparatus at a later time is positioned at or near a site in order to investigate whether or not that site is suitable for a skin invasive action, the apparatus will be able to identify the site, and based on this identification, the apparatus may decide whether or not the site is suitable for the skin invasive action.

Alternatively or additionally, the processing means may comprise means for comparing at least some of the measured parameter(s) to one or more corresponding reference parameters. This may also be used for categorising the particular area part. Thus, it may be known that specific parameters will have characteristic values depending on which body part and/or which part of a certain body part the particular area part belongs to. Thus, by comparing measured parameters to corresponding reference parameters it is possible to determine which body part and/or which part of a specific body part the particular area part belongs to.

The measuring means may comprise means for generating and emitting an acoustic wave and means for detecting an acoustic response signal. This may advantageously be in the form of an ultrasound scanner and means for detecting an ultrasound response signal, but the acoustic wave and/or the acoustic response signal may alternatively have a frequency which is outside the ultrasound frequency range. Thus, in this case the apparatus generates and emits an acoustic signal, e.g. an ultrasound signal, towards the particular area part. The signal will subsequently be at least partly reflected on an outer surface of the particular area part and/or by one or more subcutaneous layers and/or on one or more boundaries between subcutaneous layers. Thereby an acoustic response signal is created. Due to the properties of the respective surfaces, layers and boundaries in relation to reflection, scattering and absorption, the response signal will contain information relating to the particular area part, e.g. with respect to the thickness and/or composition of the individual layers. To this end an ultrasound signal is particularly suitable.

Alternatively or additionally, the measuring means may comprise means for generating and emitting an electromagnetic wave and means for detecting an electromagnetic response signal. This may advantageously be in the form of an infrared scanner and means for detecting an infrared response signal, but the electromagnetic wave and/or the electromagnetic response signal may alternatively have a frequency which is outside the infrared frequency range. The measuring procedure may be performed similarly to the procedure described above in relation to acoustic waves. However, an electromagnetic signal, in particular an infrared signal, is particularly suitable for detecting characteristics of the colouring of the skin or the location of and/or distance to blood vessels.

Alternatively or additionally, the measuring means may comprise means for generating and emitting any other suitable kind of waves or particles and means for detecting a corresponding response signal.

The apparatus may further comprise means for performing the skin invasive action. This may, e.g., be in form of an injection needle, e.g. in case the skin invasive action comprises injecting a drug into the particular area part. Alternatively or additionally, the means for performing the skin invasive action may comprise an infusion apparatus, e.g. for infusing a drug or a fluid into the mammal. Alternatively or additionally, the means for performing the skin invasive action may comprise means for collecting a blood sample, a tissue sample and/or a sample of another kind of body fluid, e.g. interstitial fluid. This may include a needle or biopsy equipment for obtaining a biopsy of one or more subcutaneous layers. Alternatively or additionally, the means for performing the skin invasive action may comprise a needle containing a sensor device for measuring one or more components of a body fluid, e.g. interstitial fluid, like a continuous plasma glucose sensor. Alternatively or additionally, the means for performing the skin invasive action may comprise any other suitable kind of device, such as a jet injector being adapted to inject a drug or a fluid into the mammal by means of a jet injection, i.e. a 'needleless' injection where the drug or fluid is injected by means of a relatively high pressure. Such devices may advantageously be used for inoculations.

At least the measuring means and the means for performing the skin invasive action may advantageously form an integrated part of the apparatus. In this case the apparatus may be an injection device, e.g. a doser pen for injecting a dose of insulin into a mammal, and the injection device may be equipped with the measuring means. Thus, when it is desired to inject a dose of insulin, the apparatus is positioned at the particular area part, this part thereby being suggested as an injection site. Subsequently the measuring means measure the relevant parameter(s), the parameter(s) is/are processed, and on the basis of the processed parameter(s) it is determined whether or not the particular area part is suitable for the injection. In case it is determined that the area part is suitable, the injection is performed immediately. In case it is determined that the area part is not suitable the apparatus is moved to another area part and the process is performed once again. The apparatus may suggest a new site as described above.

Alternatively the apparatus may be a measuring device, e.g. a device for measuring a blood glucose level. In this case the procedure is similar to the one described above. However, in this case the skin invasive action comprises obtaining a blood sample. The apparatus may in this case furthermore be adapted to analyse the blood sample after it has been obtained.

The apparatus may, alternatively, be or form part of an electronic device, such as a cell phone, a Personal Digital Assistant (PDA), a Personal Computer (PC) and/or any other suitable kind of device. Alternatively or additionally, the apparatus may be adapted to communicate with any of the kinds of devices mentioned above. Such communication may be wireless, e.g. via a Wireless Local Area Network (WLAN), a cell phone network, an infrared link, etc., or it may take place via a wired connection, such as a Local Area Network (LAN), the Internet, a direct wire connection between the devices, a Public Switched Telephone Network (PSTN), etc.

The measured parameter(s) may comprise one or more parameters relating to the surface of the particular area part. Such parameters may comprise the conductivity of the skin of the area part, colouring and/or variations in colouring of the area part, texture and/or variations in texture of the area part, and/or any other suitable parameter which relates to the surface of the area part.

Alternatively or additionally, the measured parameter(s) may comprise one or more parameters relating to one or more subcutaneous layers of the particular area part and/or to one or more boundaries between such layers. Such parameters may comprise thickness and/or variations in thickness of a layer, e.g. a fat layer, reflective properties of one or more boundaries between the layers, position and/or distance to blood vessels, position and/or distance to one or more internal organs, and/or any other suitable parameter which relates to one or more subcutaneous layers.

The mammal is preferably a human being. However, it may alternatively be another kind of mammal, e.g. a pet, such as a dog, a cat, etc.

BRIEF DESCRIPTION OF THE DRAWINGS

The invention will now be described in further detail with reference to the accompanying drawings in which.

DETAILED DESCRIPTION OF THE DRAWINGS

Figure 1:
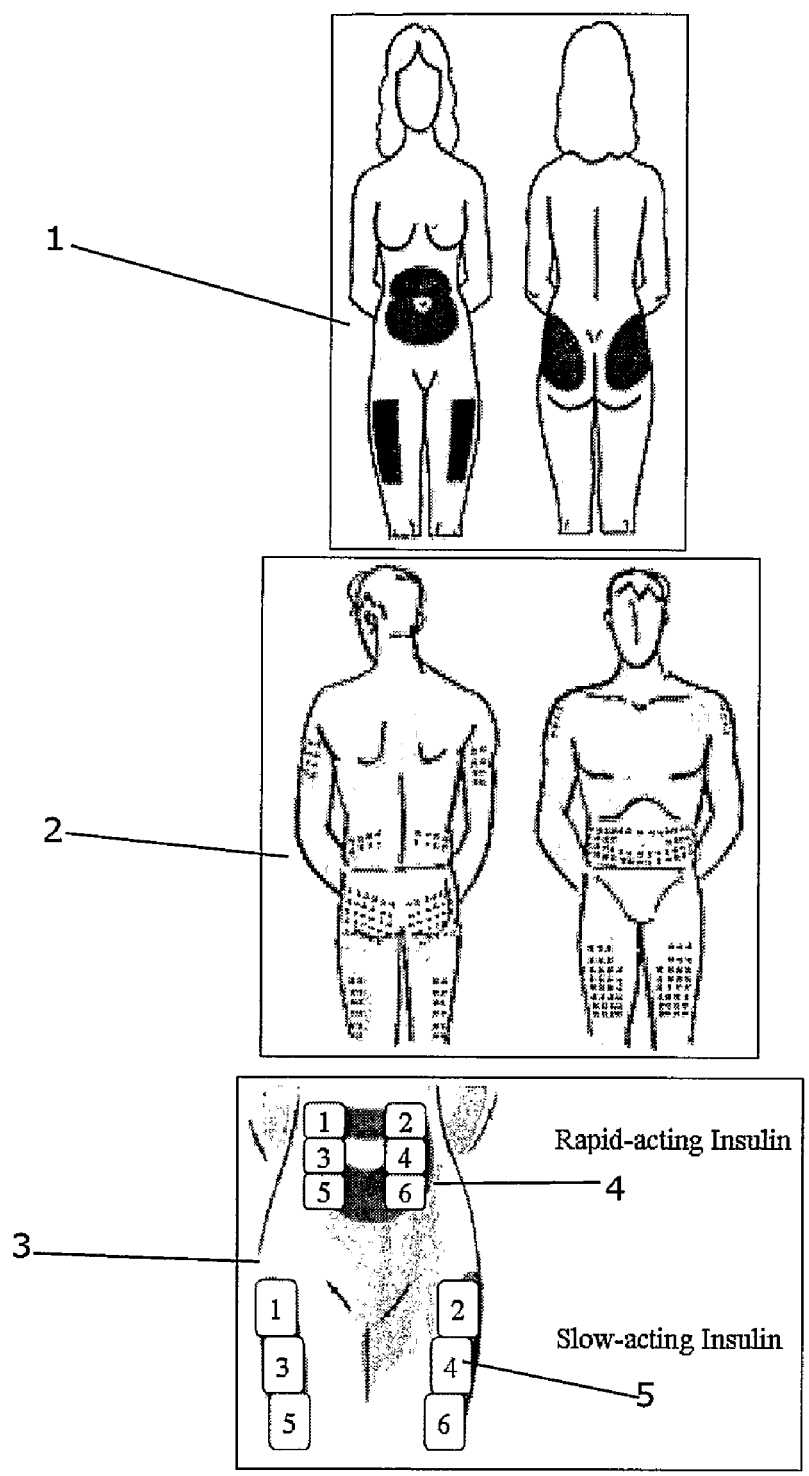
FIG. 1 shows examples of insulin injection sites for persons with diabetes.

FIG. 1 shows examples of insulin injection areas for a female 1 and a male 2. As it can be seen in the Figure, it is recommended that insulin is injected into the thighs, the stomach region or the buttocks. Furthermore, the Figure shows an example of a recommended injection pattern 3. As it can be seen, it is recommended that rapid-acting insulin is injected into the stomach region 4 and slow-acting insulin is injected into the thighs 5. It is, furthermore, recommended that injections of rapid-acting insulin are alternated between the left side and the right side of the stomach region 4, and that the exact positions of the injections are shifted in order to provide as long a period as possible between two consecutive injections at the same site. This is indicated by the increasing numbers shown in the stomach region 4. Similarly, it is recommended that injections of slow-acting insulin are alternated between the left and the right thigh 5, and that the exact positions of the injections are shifted. This is also indicated by increasing numbers.

It is cumbersome to manually keep track of an injection pattern as the one shown in FIG. 1. However, as mentioned above, the apparatus according to the present invention helps a person in keeping track of previous injection sites and in choosing a suitable site for the next injection. Furthermore, the apparatus according to the present invention can help the person during the actual injection procedure, thereby avoiding the need for separate records and allowing the person to choose a suitable injection site regardless of where the person is found to be.

Figure 2:
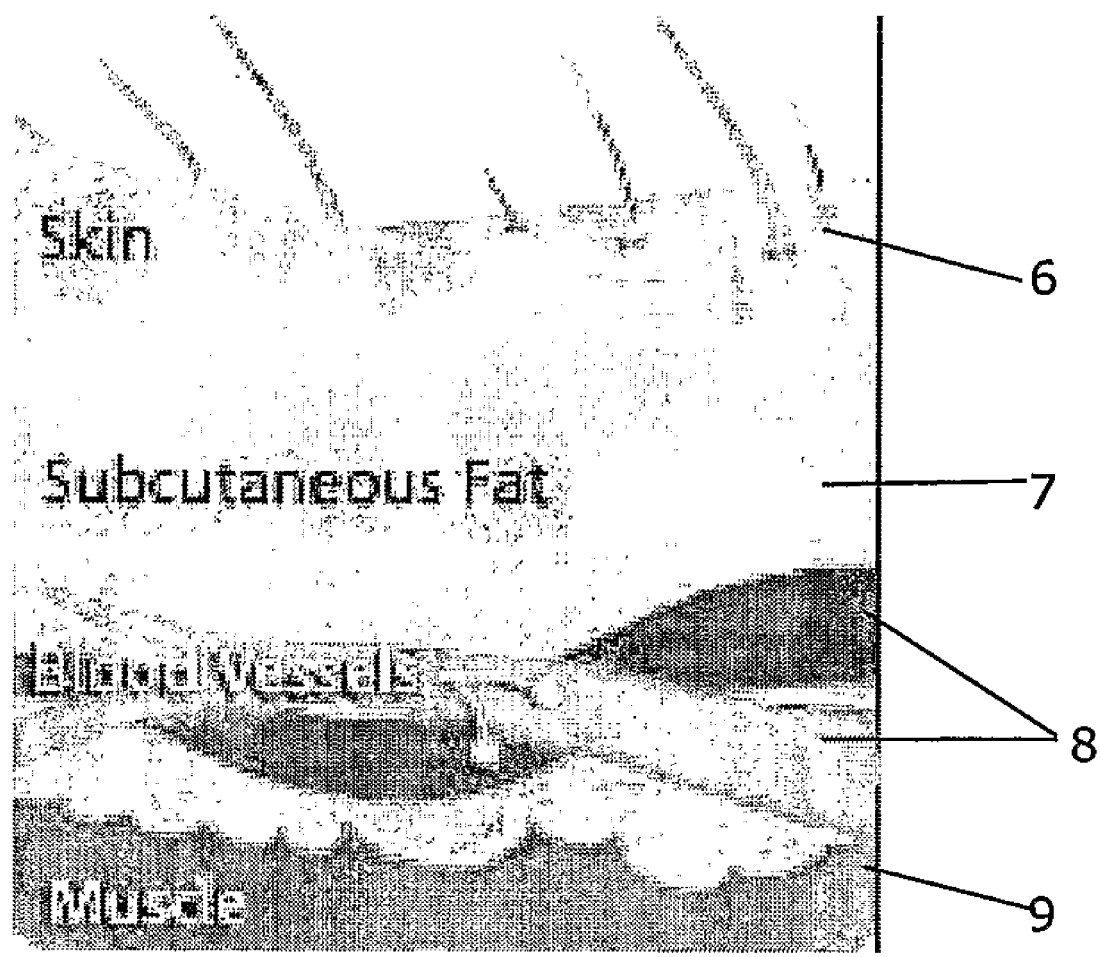
FIG. 2 shows a cross section through the skin and subcutaneous layers of a person.

FIG. 2 shows a cross section through the skin 6, a subcutaneous fat layer 7, blood vessels 8 and part of a muscle 9. Insulin should be injected into a subcutaneous fat layer 7 to absorb the insulin. It is therefore important that a site where such a layer 7 is present is chosen. This is why the sites shown in FIG. 1 are recommended for injection of insulin.

Figure 3:
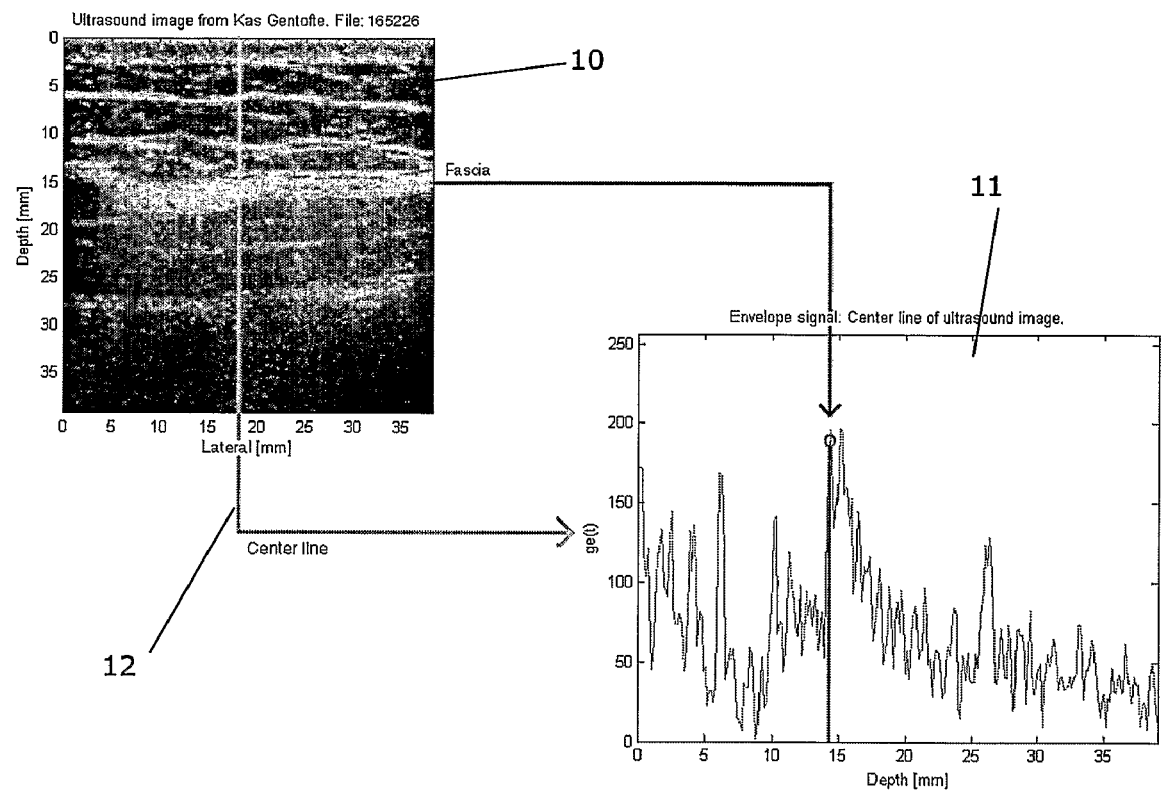
FIG. 3 shows an ultrasound image and a corresponding envelope signal of a measurement of an area part of the skin of a person.

FIG. 3 shows an ultrasound image 10 of an area part of the skin of a person. The image 10 shows a number of layers positioned at different depths, i.e. at different distances from the skin surface (corresponding to '0' at the depth scale). The layers show up in the image 10 as lighter or darker areas due to the various reflection properties of the various layers.

FIG. 3 also shows an envelope signal 11 corresponding to a centre line 12 of the ultrasound image 10. The envelope signal 11 is the signal where the carrier wave has been transformed out as a function of the depth, i.e. the distance from the surface of the skin.

Using an ultrasound image as the one shown in FIG. 3 it is possible to determine the position and thickness of the various layers, and on the basis of this it may be determined whether or not the corresponding site is suitable for the skin invasive action.

Figure 4:
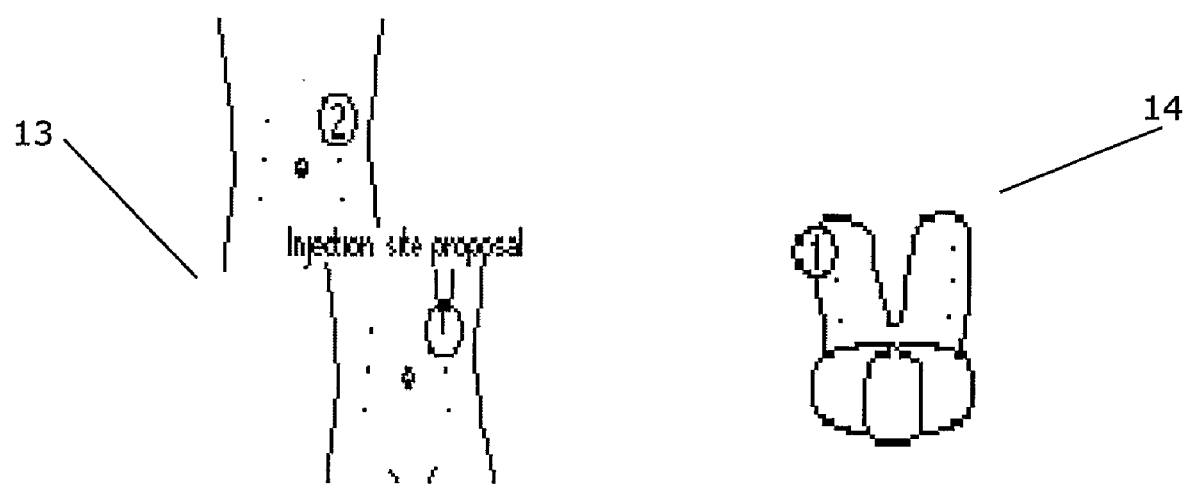
FIG. 4 shows examples of display screens of one embodiment of an apparatus according to the present invention.

FIG. 4 shows examples of display screens of one embodiment of an apparatus according to the present invention. The left display screen 13 shows a suggestion for injection site for rapid-acting insulin. On the display the suggestion is marked with a flashing needle tip or circle. The right display screen 14 shows a suggestion for injection site for slow-acting insulin. (The figure is a person sitting and seen from above. The suggested site is a position over the left knee.)

The invention claimed is:

1. An apparatus for assisting in choosing a site for a skin invasive action, the apparatus comprising:
    means for measuring one or more parameters relating to a particular area part of the skin or subcutis of a mammal,
    means for processing said parameter(s) and keeping track of sites used for a skin invasive action, thereby enabling a person to vary the chosen site,
    means for categorising the particular area part as belonging to one of at least two body parts based on the processed parameter(s), and
    means for determining whether or not the particular area part is suitable for the skin invasive action based on the processed parameter(s).

2. An apparatus according to claim 1, wherein each body part comprises at least two parts.

3. An apparatus according to claim 1, wherein the at least two body parts are represented by stomach and thigh.

4. An apparatus according to claim 1, wherein the at least two body parts are represented by at least a right part of the stomach, a left part of the stomach, the right thigh and the left thigh.

5. An apparatus according to claim 1, comprising means for indicating whether or not the particular area part is suitable for a skin invasive action.

6. An apparatus for assisting in choosing a site for a skin invasive action, the apparatus comprising:
    means for measuring one or more parameters relating to a particular area part of the skin or subcutis of a mammal,
    means for processing said parameter(s),
    means for categorising the particular area part as belonging to one of at least two body parts based on the processed parameter(s), and
    means for determining whether or not the particular area part is suitable for the skin invasive action based on the processed parameter(s) and whether or not sufficient time has lapsed since the area was last used for a skin invasive action.

7. A method for choosing a site for a skin invasive action, the method comprising:
    measuring one or more parameters relating to a particular area part of the skin or subcutis of a mammal,
    providing a processor to process said parameter(s),
    providing an apparatus to categorize the particular area part based on the processed parameter(s), and
    providing an apparatus to determine whether or not the particular area part is suitable for the skin invasive action based on the processed parameter(s), and whether or not sufficient time has lapsed since the area was last used for a skin invasive action.

8. A method according to claim 7, further comprising means for indicating whether or not the particular area part is suitable for the skin invasive action.

9. A method according to claim 8, wherein the indicating means comprises means for producing a warning signal in case it is determined that the particular area part is not suitable for the skin invasive action.

10. A method according to claim 7, wherein the processing means comprises means for comparing at least some of the measured parameter(s) to one or more previously measured corresponding parameters.

11. A method according to claim 7, wherein the processing means comprises means for comparing at least some of the measured parameter(s) to one or more corresponding reference parameters.

12. A method according to claim 7, wherein the measuring means comprises means for generating and emitting an acoustic wave and means for detecting an acoustic response signal.

13. A method according to claim 12, wherein the measuring means comprises an ultrasound scanner and means for detecting an ultrasound response signal.

14. A method according to claim 7, wherein the measuring means comprises means for generating and emitting an electromagnetic wave and means for detecting an electromagnetic response signal.

15. A method according to claim 14, wherein the measuring means comprises an infrared scanner and means for detecting an infrared response signal.

16. A method according to claim 7, further comprising means for performing the skin invasive action.

17. A method according to claim 16, wherein the means for performing the skin invasive action comprises an injection needle.

18. A method according to claim 16, wherein the means for performing the skin invasive action comprises an infusion apparatus.

19. A method according to claim 16, wherein the means for performing the skin invasive action comprises means for collecting a blood sample and/or a tissue sample.

20. A method according to claim 7, wherein at least the measuring means and the means for performing the skin invasive action form an integrated part of the apparatus.

21. A method according to claim 7, wherein the measured parameter(s) comprise(s) one or more parameters relating to the surface of the particular area part.

22. A method according to claim 7, wherein the measured parameter(s) comprise(s) one or more parameters relating to one or more subcutaneous layers of the particular area part and/or to one or more boundaries between such layers.

23. A method according to claim 7, wherein the mammal is a human being.

24. A method according to claim 7, further comprising producing a warning signal in case it is determined that the particular area part is not suitable for the skin invasive action.

25. A method according to claim 7, further comprising identifying the particular area part based on the processed parameter(s).

26. A method according to claim 7, wherein the particular area is categorized as belonging to one of at least two body parts based on the processed parameter(s).

27. A method according to claim 26, wherein each body part comprises at least two parts.

28. A method according to claim 26, wherein the at least two body parts are represented by stomach and thigh.

29. A method according to claim 26, wherein the at least two body parts are represented by at least a right part of the stomach, a left part of the stomach, the right thigh and the left thigh.

30. A method according to claim 7, further comprising indicating whether or not the particular area part is suitable for a skin invasive action.

31. A method for choosing a site for a skin invasive action, the method comprising:
   providing an apparatus to measure one or more parameters relating to a particular area part of the skin or subcutis of a mammal,
   providing an apparatus to determine whether or not the particular area part is suitable for the skin invasive action based on the processed parameter(s),
   providing a processor to process said parameter(s) and keep track of sites used for a skin invasive action, thereby enabling a person to vary the chosen site, and
   providing an apparatus to categorize the particular area part based on the processed parameter(s).

* * * * *